United States Patent
Ikuta

(10) Patent No.: US 10,506,922 B2
(45) Date of Patent: Dec. 17, 2019

(54) SPECTROMETER FOR COLOR SPECTRALLY-ENCODED ENDOSCOPY

(71) Applicant: CANON USA, INC., Melville, NY (US)

(72) Inventor: Mitsuhiro Ikuta, Cambridge, MA (US)

(73) Assignee: CANON U.S.A., Inc., Melville, NY (US)

( * ) Notice: Subject to any disclaimer, the term of this patent is extended or adjusted under 35 U.S.C. 154(b) by 126 days.

(21) Appl. No.: 15/947,477

(22) Filed: Apr. 6, 2018

(65) Prior Publication Data

US 2019/0307321 A1    Oct. 10, 2019

(51) Int. Cl.

| | |
|---|---|
| *G01J 3/00* | (2006.01) |
| *A61B 1/07* | (2006.01) |
| *A61B 5/00* | (2006.01) |
| *G01J 3/02* | (2006.01) |
| *G01J 3/28* | (2006.01) |
| *G01N 21/55* | (2014.01) |
| *G01N 21/63* | (2006.01) |

(52) U.S. Cl.
CPC .............. *A61B 1/07* (2013.01); *A61B 5/0084* (2013.01); *G01J 3/0208* (2013.01); *G01J 3/2823* (2013.01); *G01J 3/024* (2013.01); *G01J 3/0218* (2013.01); *G01N 21/55* (2013.01); *G01N 21/63* (2013.01); *G01N 2201/084* (2013.01)

(58) Field of Classification Search
CPC ...... G01J 3/02; G01J 3/28; G01J 3/42; G01N 21/31; G01N 21/552
USPC ......................................................... 356/300
See application file for complete search history.

(56) References Cited

U.S. PATENT DOCUMENTS

| | | |
|---|---|---|
| 4,965,441 A | 10/1990 | Picard |
| 6,341,036 B1 | 1/2002 | Tearney et al. |

(Continued)

FOREIGN PATENT DOCUMENTS

| | | |
|---|---|---|
| JP | 1993/5-157628 A | 6/1993 |
| JP | 1994/6-233198 A | 8/1994 |

(Continued)

OTHER PUBLICATIONS

Kang, D., et al., "Minature grating for spectrally-encoded endoscopy", Lab Chip, 2013, pp. 1810-1816, vol. 13.

(Continued)

*Primary Examiner* — Md M Rahman
(74) *Attorney, Agent, or Firm* — Canon U.S.A., Inc., IP Division

(57) ABSTRACT

A grating element has an interface configured to cause light beams, include N visible color lights, incident to the interface to diffract at different orders. An imaging lens is configured to focus the N visible color lights diffracted by the grating element. A sensor is configured to receive and detect the focused N visible color lights. The focused N visible color lights include at least a first color light and a second color light. The first color light is diffracted in a first diffraction order and corresponds to a first wavelength resolution for the first color light. The second color light is diffracted in a second diffraction order and corresponds to a second wavelength resolution for the second color light. The first diffraction order is higher than the second diffraction order and the first wavelength resolution is smaller than the second wavelength resolution.

21 Claims, 6 Drawing Sheets

(56) References Cited

U.S. PATENT DOCUMENTS

| | | | |
|---|---|---|---|
| 7,447,408 B2 | 11/2008 | Bouma et al. | |
| 7,551,293 B2 | 6/2009 | Yelin et al. | |
| 7,796,270 B2 | 9/2010 | Yelin et al. | |
| 7,843,572 B2 | 11/2010 | Tearney et al. | |
| 7,847,949 B2 | 12/2010 | Tearney et al. | |
| 7,859,679 B2 | 12/2010 | Bouma et al. | |
| 7,889,348 B2 | 2/2011 | Tearney et al. | |
| 8,045,177 B2 | 10/2011 | Tearney et al. | |
| 8,145,018 B2 | 3/2012 | Shishkov et al. | |
| 8,812,087 B2 | 8/2014 | Yelin et al. | |
| 8,838,213 B2 | 9/2014 | Tearney et al. | |
| 8,917,390 B2 | 12/2014 | Behr et al. | |
| 9,046,419 B2 | 6/2015 | Yelin et al. | |
| 9,254,089 B2 | 2/2016 | Tearney et al. | |
| 9,295,391 B1 | 3/2016 | Tearney et al. | |
| 9,415,550 B2 | 8/2016 | Tearney et al. | |
| 9,557,154 B2 | 1/2017 | Tearney et al. | |
| 2003/0223248 A1* | 12/2003 | Cronin | G01J 3/10 362/555 |
| 2011/0237892 A1* | 9/2011 | Tearney | A61B 5/0062 600/160 |
| 2012/0101374 A1 | 4/2012 | Tearney et al. | |
| 2014/0354802 A1 | 12/2014 | Ohtomo et al. | |
| 2016/0206184 A1 | 7/2016 | Tearney et al. | |
| 2016/0341951 A1 | 11/2016 | Tearney et al. | |
| 2016/0349417 A1 | 12/2016 | Tearney et al. | |
| 2017/0035281 A1 | 2/2017 | Takeuchi et al. | |
| 2017/0167861 A1 | 6/2017 | Chen et al. | |
| 2017/0168232 A1 | 6/2017 | Tearney et al. | |
| 2017/0176736 A1 | 6/2017 | Yamamoto et al. | |
| 2017/0290492 A1 | 10/2017 | Hamm et al. | |
| 2017/0322079 A1 | 11/2017 | Do et al. | |

FOREIGN PATENT DOCUMENTS

| | | |
|---|---|---|
| JP | 2011023203 A | 2/2011 |
| WO | 2015/116939 A1 | 8/2015 |
| WO | 2015/116951 A2 | 8/2015 |
| WO | 2017/024145 A1 | 2/2017 |
| WO | 2017/117203 A1 | 7/2017 |
| WO | 2017/139657 A1 | 8/2017 |
| WO | 2017/165511 A1 | 9/2017 |

OTHER PUBLICATIONS

Kang, D., et al., "Spectrally-encoded color imaging", Optics Express, Aug. 17, 2009, pp. 15239-15247, vol. 17, No. 17.

Yelin, D., et al., " Three-dimensional miniature endoscopy", Nature, Oct. 19, 2006, p. 765, vol. 443.

Zeidan, A et al. "Miniature forward-viewing spectrally encoded endoscopic probe", Optics Letters, Aug. 15, 2014, pp. 4871-4874, vol. 39, Issue 16.

\* cited by examiner

SPECTROMETER FOR COLOR SPECTRALLY-ENCODED ENDOSCOPY

BACKGROUND OF THE INVENTION

Field of the Invention

One disclosed aspect of the embodiments relates to spectrally-encoded endoscopy (SEE).

Description of the Related Art

An endoscopy is a procedure in which a doctor uses specialized instruments to view and operate on the internal organs of a patient's body. Spectrally-encoded endoscopy (SEE) is an ultraminiature endoscopy technology that acquires high-definition images of internal organs through a sub-mm endoscopic probe. In SEE, a grating at the tip of the imaging optics diffracts the broadband light into multiple beams, where each beam with a distinctive wavelength is illuminated on a unique transverse location of the tissue. By encoding one transverse coordinate with the wavelength, SEE can image a line of the tissue at a time without using any beam scanning devices. The probe typically receives light from a light source through an optical fiber and may have optical components to illuminate a sample (e.g., internal organs of a patient's body). The light is then reflected or scattered and collected by an optical guide. The optical guide then carries or guides the reflected or scattered light to a spectrometer which analyzes the light and provides information on the sample such as images representative of the biological structure of the sample.

A diffraction grating is an optical component with a periodic structure, which may include grooves that are spaced by a distance d apart. The periodic structure splits and diffracts light into several beams travelling in different directions. A light ray of wavelength $\lambda$ incident at an angle $\alpha$ and diffracted by a grating of groove spacing d along a number of angles $\beta_m$. The relationship among the angles and the groove distance may be described by the following equation:

$$-m\lambda = d(n_i \sin \alpha + n_d \sin \beta) \quad (1)$$

where $n_i$ and $n_d$ are refractive indices of the material where the ray is incident and diffracted, respectively, and m is referred to as the diffraction order, or spectral order, and is an integer.

A spectrometer is an instrument to measure properties of light over a portion of the electromagnetic spectrum. When the spectrometer is used together with the SEE, the assembly provides a means to visualize and analyze the spectrally encoded information in an effective manner.

Color SEE has been constructed to provide useful information to distinguish different biological samples or elements such as arteries and veins. Conventional spectrometers with color SEE typically detect red, green, blue (RGB) light beams. The RGB light beams are detected having the same diffraction orders. This results in the resolution for color SEE not being as high as in previous spectrometers.

SUMMARY OF THE INVENTION

A spectrometer has a grating element that has an interface or a surface configured to cause light beams incident to the interface or surface to diffract in different orders. The light beams include N visible color lights where N is an integer equal to or greater than 2. An imaging lens is configured to focus the N visible color lights diffracted by the grating element. A sensor is configured to receive and detect the N visible color lights focused by the imaging lens. The focused N visible color lights include at least a first color light and a second color light. The first color light is diffracted in a first diffraction order and corresponds to a first wavelength resolution for the first color light. The second color light is diffracted in a second diffraction order and corresponds to a second wavelength resolution for the second color light. The first diffraction order is higher than the second diffraction order and the first wavelength resolution is smaller than the second wavelength resolution. Here, the phrase "the diffraction order is higher (or lower)" means "the absolute value of the diffraction order is higher (or lower)."

Further features of the disclosure will become apparent from the following description of exemplary embodiments with reference to the attached drawings.

DESCRIPTION OF THE EMBODIMENTS

One disclosed aspect of the embodiments includes an optical subsystem in a spectrometer which is configured such that a higher diffraction order is used for the blue light than for the red light. This configuration renders higher resolution for blue than red.

Figure 1:
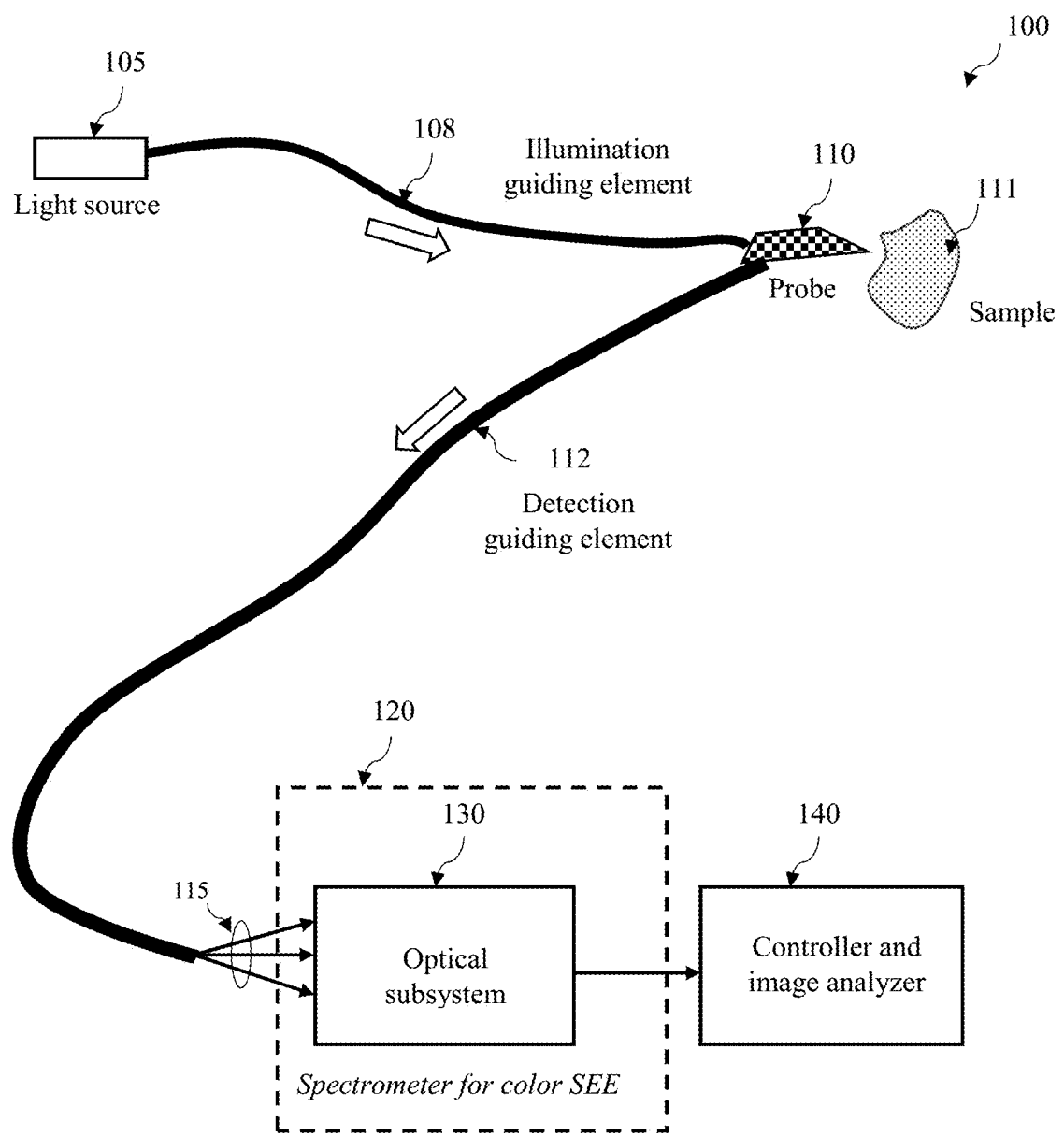
FIG. 1 is a diagram illustrating a system for color spectrally encoded endoscopy (SEE).

FIG. 1 is a diagram illustrating a system 100 for color spectrally encoded endoscopy (SEE). The system 100 includes a light source 105, an illumination guiding element 108, a probe 110, a sample 111, a detection guiding element 112, a spectrometer 120 for color SEE, and a controller and image analyzer 140. The spectrometer 120 includes an optical subsystem 130. It may also include part or all of the controller and image analyzer 140. The system 100 may include more or less than the above components.

The light source 105 generates light beams from a broadband light which may span visible color spectrum. The visible color spectrum may include red, green, and blue lights which occupy wavelength bands of approximately 620 nm-780 nm, 495 nm-585 nm, and 408 nm-495 nm, respectively. The light source 105 may be any optical source that emits light. Examples include fluorescent lamp, incandescent (e.g., tungsten) lamp, solid state lighting (SSL) such as light emitting diode (LED), phosphor-converted light-emitting diode (PCLED), and organic light emitting diode (OLED), and laser diodes, and supercontinuum laser. The light beams may be guided by the illumination guiding component 108 such as an optical fiber or a slit. The optical fiber may be a single-mode fiber, multi-mode fiber, or a double clad fiber. The probe 110 receives the light beams from the illumination guiding component 108 and illuminates the sample 111 by the light beams. The probe 110 may have appropriate optical components to provide the illuminating light beams to the sample 111. The probe 110 may be rotated or moved around the sample 111. The sample 111 may be a biological sample, a tissue, or in vivo sample. The sample 111 may reflect or scatter the illuminating light from the probe. The detection guiding element 112 collects the reflected or scattered light from the sample 111 and carries or transmits the light beams to the spectrometer 120 as light beams 115.

The spectrometer 120 is an instrument or device to measure or display images of light components over the visible color spectrum. The spectrometer 120 is used for SEE applications. Therefore, the images reflect properties of biological components of a human being (e.g., a patient) that the spectrometer 120 is measuring, acquiring, detecting, or displaying. For brevity, components related to the SEE and are not necessary for the understanding of the embodiments are not described further. These components may include probe, scanner, optical filter, mirror, reflector, etc.

The optical subsystem 130 includes optical components that provides high-resolution images of detected color lights from the light beams 115. It is understood that the probe 110 is typically applied to a human body to examine a sample inside the human body. For brevity and clarity, this set-up is not shown. The controller and image analyzer 140 may operate independently or be partially or fully included in the spectrometer 120. It collects the images of the color lights from the optical subsystem 130, analyzes the images, calculates relevant quantities such as pixel intensity, and displays the images on a display device. The controller and image analyzer 140 may also provide control functions to the optical subsystem, such as control movement and/or alignment of optical components (e.g., lenses, sensors).

Figure 2:
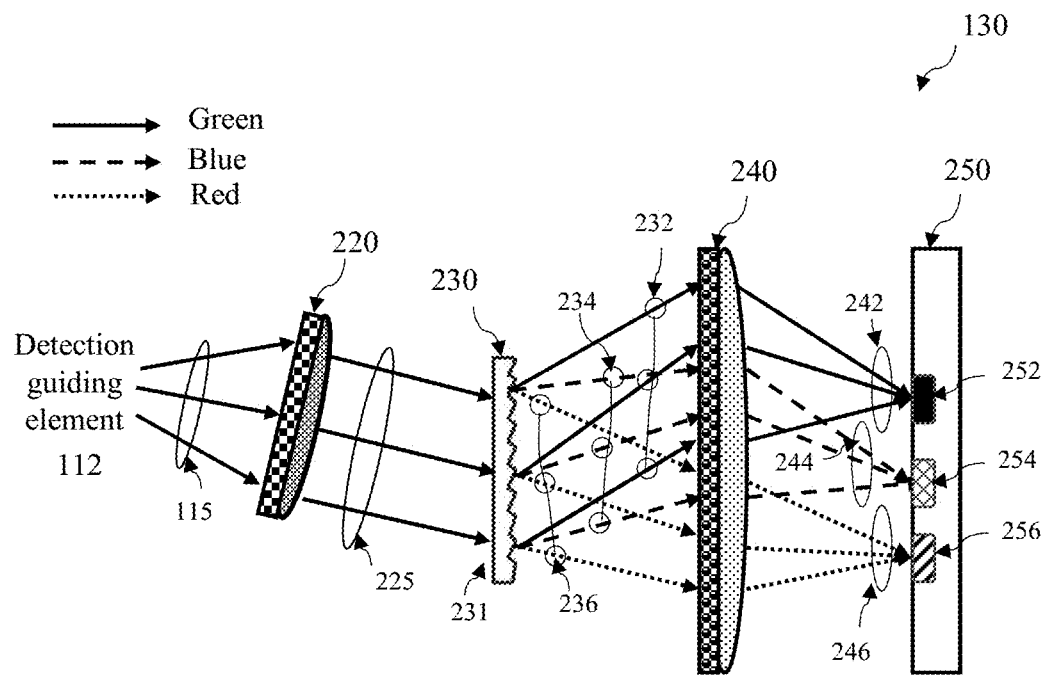
FIG. 2 is a diagram illustrating an optical subsystem for the color SEE according to a first embodiment.

FIG. 2 is a diagram illustrating the optical subsystem 130 shown in FIG. 1 for the color SEE according to a first embodiment. The optical subsystem 130 has a number of components whose parameters may be designed, selected, or configured to achieve the desired results as discussed in the following. It includes a collimation lens 220, a grating element 230, an imaging lens 240, and a sensor 250. The optical subsystem 130 may include more or less than the above components.

The collimation lens 220 collimates the light beams 115 into collimated light beams 225. The collimation lens 220 has a focal length. The focal length of the collimation lens 220 may be selected together with other parameters to give the desired overall effects. In one embodiment, the collimation lens 220 may be fixed and its focal length is not used as part of the configuration of the optical system 130.

Similar to the collimation lens 220, the grating element 230, the imaging lens 240, and the sensor 250 may have parameters that may be designed or selected to provide desirable results.

The grating element 230 has an interface or a surface 231 configured to cause the light beams 225 incident to the interface or surface 231 to diffract in different orders. The light beams 225 including N visible color lights where N is an integer equal to or greater than 2. The grating element 230 may employ any suitable grating technique such as binary grating, blazed grating, or holographic grating. The grating element 230 may have a groove density which is a parameter selected as part of the configuration of the optical subsystem to provide the desired results. For example, the grating element 230 may be binary grating of silica with 1.7 µm depth and 0.4 duty cycle, and the groove density is 820 lines/mm. In this case, the minimum diffraction efficiency is 0.36.

As an illustration example, suppose the light beams 225 include a red light, a green light, and a blue light. The grating element 230 causes these lights to diffract into three groups 232, 234, and 236. Note that the grouping of the diffracted lights is in terms of the direction or color of the lights and not the location of the diffraction. The three groups 232, 234, and 236 includes three green, blue, and red lights, respectively, diffracted in predetermined diffraction orders.

The imaging lens 240 is configured to focus the N visible color lights diffracted by the grating element 230. In the above example, the focused three groups of visible color lights from the imaging lens 240 are formed into three groups 242, 244, and 246. Each group corresponds to a color. The three groups 242, 244, and 246 are focused and directed to the sensor 250 into three colors green, blue, and red, respectively. Each of the color lights has a diffraction order as a result of the grating element 230 and the imaging lens 240 and a wavelength resolution.

The sensor 250 is configured to receive and detect the N visible color lights focused by the imaging lens 240. In the above example, the three detected lights are formed and arranged on the sensor 250 in three bands 252, 254, and 256 that correspond to green, blue, and red lights, respectively.

The configuration of the optical subsystem is such that the diffraction order of the blue light is higher than the diffraction order of the red light. When this is achieved, the spectrometer will have a higher resolution for the blue light (or smaller wavelength resolution) than the red light because the blue light is more dispersed on the sensor than the red light.

Figure 3:
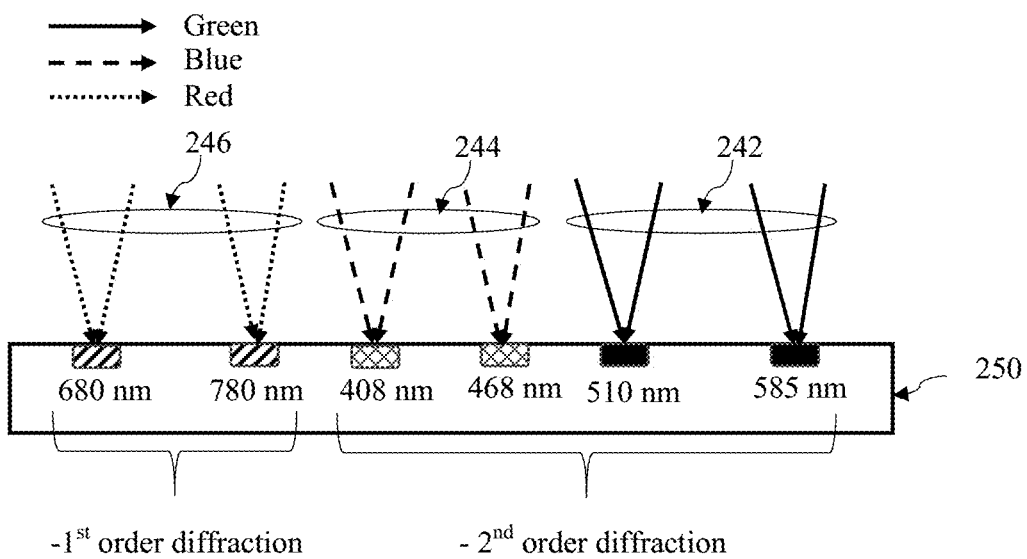
FIG. 3 is a diagram illustrating an arrangement of color lights as received and detected on the sensor according to a first embodiment.

FIG. 3 is a diagram illustrating an arrangement of color lights as received and detected on the sensor according to a first embodiment. The arrangement shows the $-1^{st}$ order diffraction and $-2^{nd}$ order diffraction. The $-1^{st}$ order diffraction includes the red light group 246 from 680 nm to 780 nm. The $-2^{nd}$ order diffraction includes the blue light group 244 from 408 nm to 468 nm and the green light group 242 from 510 nm to 585 nm.

As an example with numerical values, suppose the optical subsystem 130 has the following selected parameters. The focal length of the collimation lens 220 is 100 mm, the focal length of the imaging lens 240 is 50 mm, the groove density of the grating element 230 is 820 lines/mm, the diameter of the input fiber core for guiding the light beams 115 is 90 µm, and the incident angle on the grating is 22.92 degrees.

The wavelength at Littrow configuration is 950 nm in the $-1^{st}$ order, but at the same time it is 475 nm in the $-2^{nd}$ order. Light of 680 nm-780 nm is diffracted on to the line sensor in the $-1^{st}$ order, while light of 408 nm-468 nm and 510 nm-585 nm is diffracted in the $-2^{nd}$ order. So, light is coming on the sensor 250 so that the blue channel light is between the red and green channel lights as shown in FIG. 3.

The ideal wavelength resolution $\Delta\lambda$ of the spectrometer is given by $$\Delta\lambda = \frac{\cos\theta_i}{-mG} \frac{a}{f_{col}} \quad (2)$$

where G is groove density of the grating, m is diffraction order, $f_{col}$ is focal length of collimation lens, $\theta_i$ is incident angle, and α is input fiber core diameter. The wavelength resolution for the red light (680 nm-780 nm) is 1.01 nm, and that for blue and green lights is 0.51 nm.

It should be noted that the lights in the bands of 468 nm-510 nm (between blue and green) and 585 nm-680 nm (green and red) are not used for imaging. In this spectrometer configuration, a wide range between the green and red bands is not coming at the center on sensor but at the edge. Therefore, the sensor active area may be used more efficiently.

Figure 4:
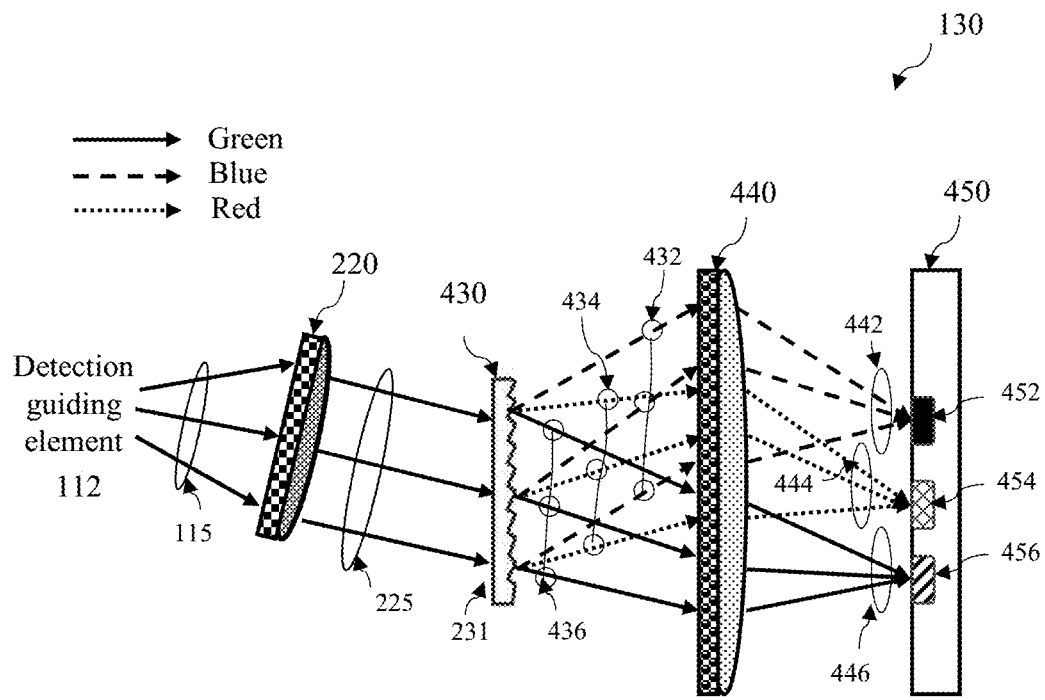
FIG. 4 is a diagram illustrating an optical subsystem for the color SEE according to a second embodiment.

FIG. 4 is a diagram illustrating the optical subsystem 130 for the color SEE according to a second embodiment. The optical subsystem 130 in FIG. 4 is similar to the optical subsystem 130 in FIG. 2 except that the color lights are diffracted in different diffraction orders. For brevity and clarity, components that are the same have the same numeral references and are not described further.

The optical subsystem 130 includes the collimation lens 220, a grating element 430, an imaging lens 440, and a sensor 450. The collimation lens 220 in FIG. 4 is similar to that in FIG. 2.

As in the first embodiment shown in FIG. 2, the parameters of the individual components are designed or selected to provide different diffraction orders. The optical subsystem 130 may include more or less than the above components.

As an illustration example, suppose the light beams 225 include a red light, a green light, and a blue light. The grating element 430 cause these lights to diffract into three groups 432, 434, and 436. As before, the grouping of the diffracted lights is in terms of the direction or color of the lights and not the location of the diffraction. The three groups 432, 434, and 436 includes three blue, red, and green lights, respectively, diffracted in predetermined diffraction orders.

The imaging lens 440 is configured to focus the N visible color lights diffracted by the grating element. In the above example, the focused three groups of visible color lights from the imaging lens 440 are formed into three groups 442, 444, and 446. Each group corresponds to a color. The three groups 442, 444, and 446 are focused and directed to the sensor 450 into three colors blue, red, and green, respectively. Note that the arrangement of the color lights are different from that in FIG. 2. Each of the color lights has a diffraction order as a result of the grating element 430 and the imaging lens 440 and corresponds to a wavelength resolution. The optical subsystem 425 is configured so that the green light in the band 510 nm-585 nm and the red light in the band 680 nm-780 nm are diffracted on to the line sensor in the same $-1^{st}$ order, while the blue light in the band 408-468 is diffracted in the $-2^{nd}$ order. In other words, the diffraction order of the blue light is higher than both the diffraction orders of the green and red lights.

In this example, the focal length of the collimation lens 120 is 150 mm, the focal length of the imaging lens 430 is 50 mm, the groove density of the grating element 430 is 820 lines/mm. The diameter of input fiber core is 90 μm. The incident angle on the grating element 430 is 17.42 degrees. The wavelength at the Littrow configuration is 730 nm in the $-1^{st}$ order, but at the same time it is 365 nm in the $-2^{nd}$ order.

The three detected lights are formed and arranged on the sensor 450 in three bands 452, 454, and 456 that correspond to blue, red, and green, respectively.

Figure 5:
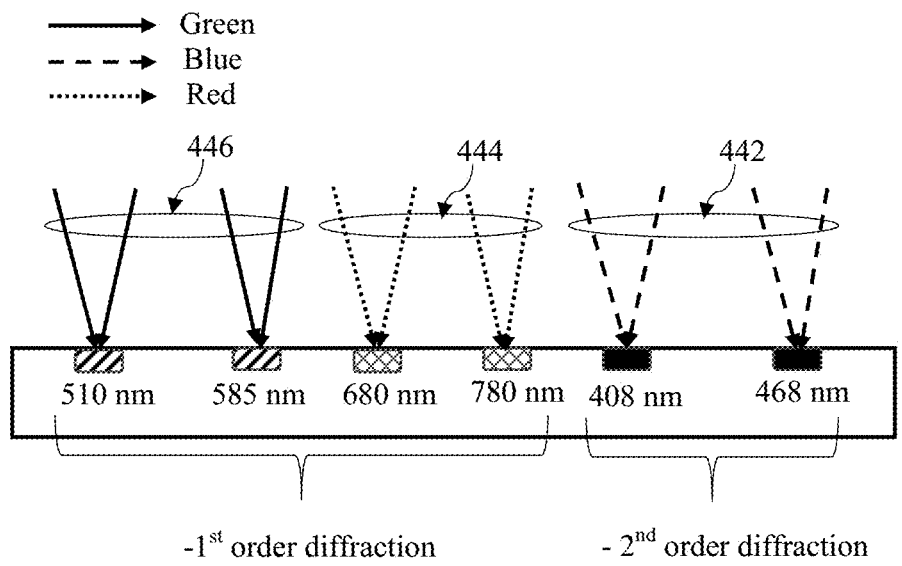
FIG. 5 is a diagram illustrating an arrangement of color lights as received and detected on the sensor according to a second embodiment.

FIG. 5 is a diagram illustrating an arrangement of color lights as received and detected on the sensor 450 according to a second embodiment.

The arrangement shows the $-1^{st}$ order diffraction and $-2^{nd}$ order diffraction. The $-1^{st}$ order diffraction includes the green light group 446 from 510 nm to 585 nm and the red light group from 580 nm to 780 nm. The $-2^{nd}$ order diffraction includes the blue light group 442 from 408 nm to 468 nm.

Figure 6:
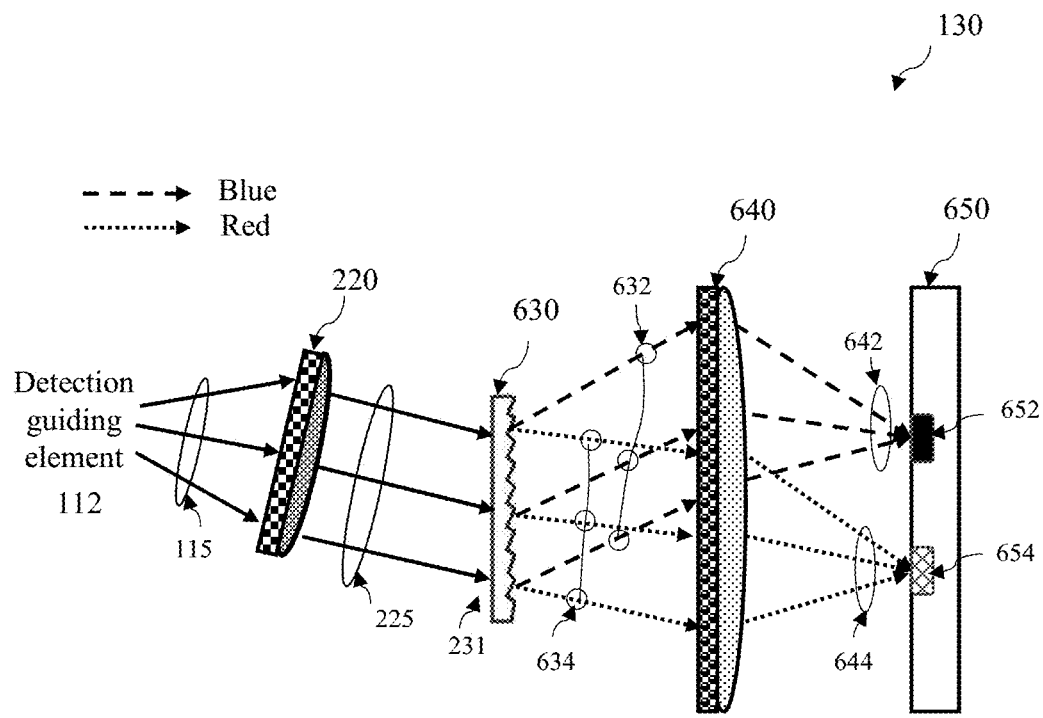
FIG. 6 is a diagram illustrating an optical subsystem for the color SEE according to a third embodiment.

FIG. 6 is a diagram illustrating an optical subsystem 130 for the color SEE according to a third embodiment. As in the second embodiment, the third embodiment has similar components as the first embodiment in FIG. 2 except that there are only two color lights as in a bi-channel SEE. For brevity and clarity, components that are the same have the same numeral references.

The optical subsystem 130 includes the collimation lens 220, a grating element 630, an imaging lens 640, and a sensor 650. The collimation lens 220 in FIG. 6 is similar to that in FIG. 2. The configuration optical assembly 425 may include more or less than the above components.

The light beams 225 include a red light and a blue light. The grating element 630 causes these lights to diffract into two groups 632 and 634. The two groups 632 and 634 include two blue and red lights, respectively, diffracted in predetermined diffraction orders.

The imaging lens 640 is configured to focus the N visible color lights diffracted by the grating element. In the above example, the focused two groups of visible color lights from the imaging lens 640 are formed into two groups 642 and 644. Each group corresponds to a color. The two groups 642 and 644 are focused and directed to the sensor 650 into two colors blue and red, respectively. Note that the arrangement of the color lights are different from that in FIGS. 2 and 4. Each of the color lights is diffracted in a diffraction order as a result of the grating element 630 and the imaging lens 640 and corresponds to a wavelength resolution. The bi-channel SEE probe may be configured so that the blue light in the band 450 nm-550 nm is diffracted in the $-3^{rd}$ order and the red light in the band 675 nm-825 nm is diffracted in the $-2^{nd}$ order. In another embodiment, the optical subsystem 625 is configured so that the blue light in the band 450 nm-550 nm is diffracted in the $-2^{nd}$ order and the red light in the band 675 nm-825 nm is diffracted in the $-1^{st}$ order.

In other words, the diffraction order of the blue light is higher than the diffraction order of the red light.

In this example, the focal length of the collimation lens 120 is 150 nm, the focal length of the imaging lens 430 is 550 nm, the groove density of the grating element 630 is Boo lines/mm. The diameter of input fiber core is 90 μm. The incident angle on the grating element 430 is 20.85 degrees. The wavelength at the Littrow configuration is 890 nm in the $-1^{st}$ order, but at the same time it is 445 nm in the $-2^{nd}$ order.

The two detected lights are formed and arranged on the sensor 650 in two bands 652 and 654 that correspond to blue and red, respectively.

Figure 7:
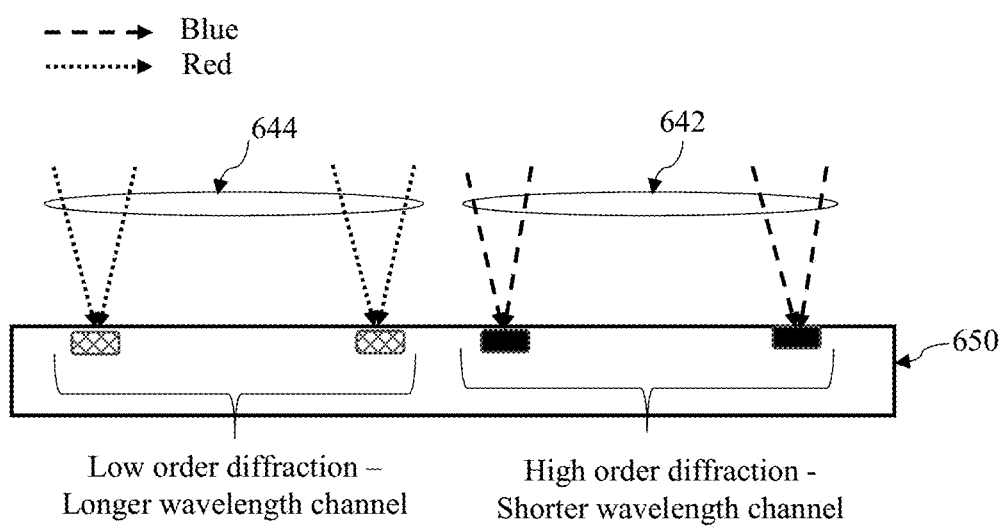
FIG. 7 is a diagram illustrating an arrangement of color lights as received and detected on the sensor according to a third embodiment.

FIG. 7 is a diagram illustrating an arrangement of color lights as received and detected on the sensor 650 according to a third embodiment.

The arrangement shows the low order diffraction (or longer wavelength channel) and the high order diffraction (or shorter wavelength channel). The low order diffraction includes the red light group 644 from 675 nm to 825 nm and the blue light group from 450 nm to 550 nm.

Figure 8:
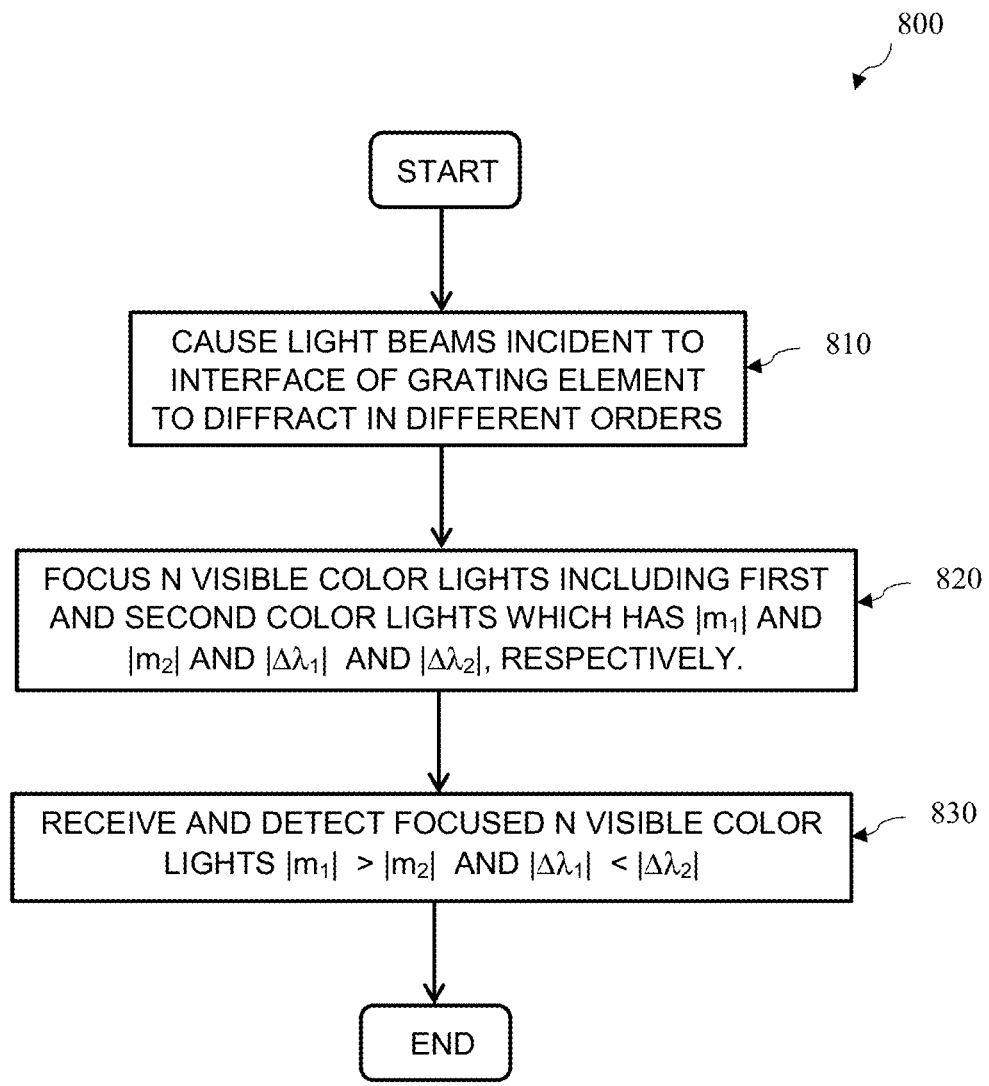
FIG. 8 is a diagram illustrating a process for high resolution spectrometer for color SEE.

FIG. 8 is a diagram illustrating a process Boo for high resolution spectrometer for color SEE.

Upon START, the process Boo causes light beams incident to a surface of a grating element to diffract at different orders (Block 810). The light beams include N visible color lights where N is an integer equal to or greater than 2. Then, the process Boo focuses, by an imaging lens, the N visible color lights diffracted by the grating element (Block 820). The focused N visible color lights include at least a first color light and a second color light. The first color light has a first diffraction order and a first wavelength resolution. The second color light has a second diffraction order and a second wavelength resolution. Next, the process 800 receives and detects, by a sensor, the N visible color lights focused by the imaging lens (Block 830). The first diffraction order is higher than the second diffraction order and the first wavelength resolution is smaller than the second wavelength resolution. The process Boo is then terminated.

Figure 9:
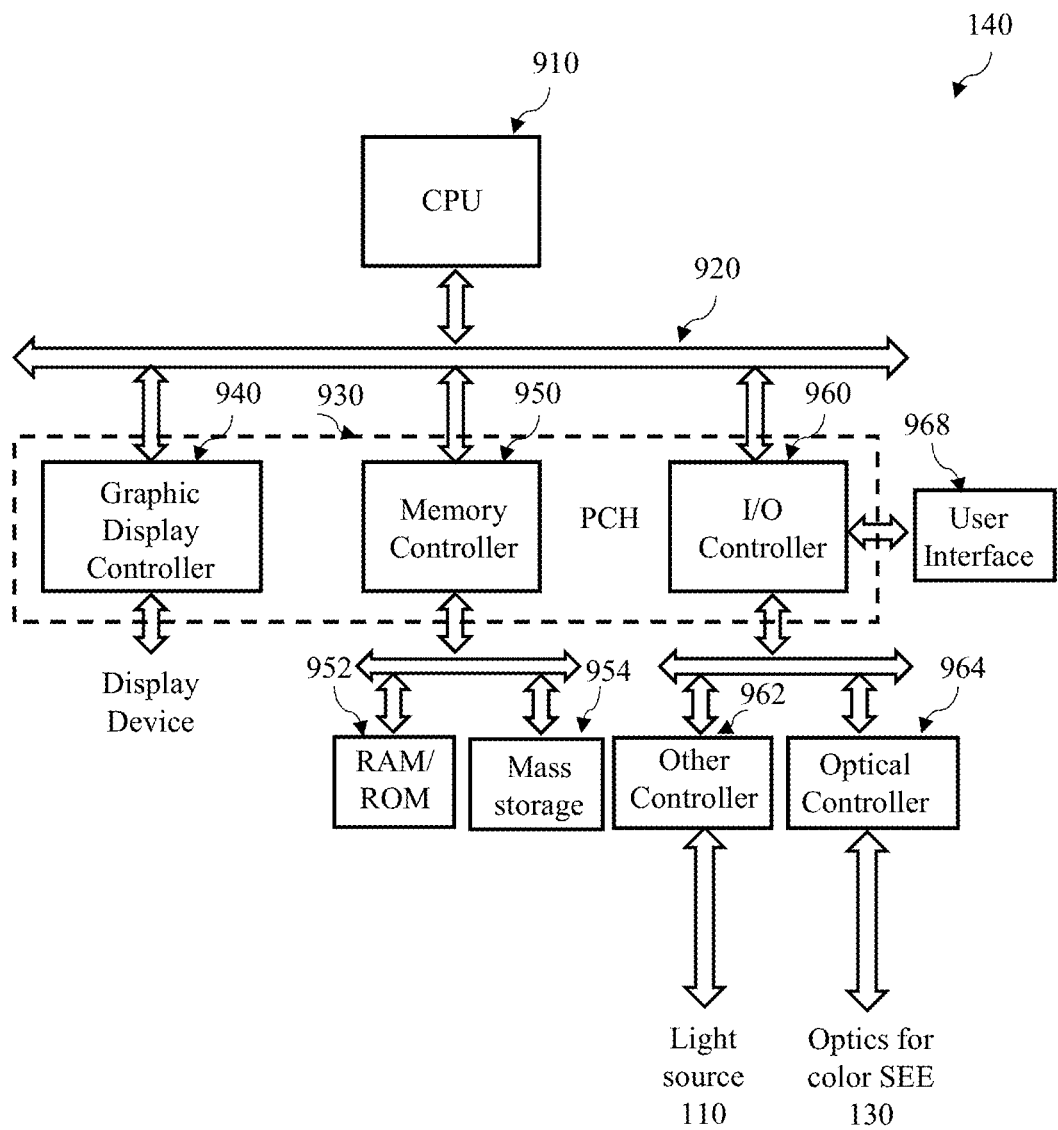
FIG. 9 is a diagram illustrating an image analyzer of the spectrometer for color SEE.

FIG. 9 is a diagram illustrating the image analyzer 140 shown in FIG. 1 of the spectrometer for color SEE.

The system or image analyzer 140 includes a central processing unit (CPU) or a processor 910, a platform controller hub (PCH) 930, and a bus 920. The PCH 930 may include a graphic display controller (GDC) 940, a memory controller 950, an input/output (I/O) controller 960, and a mass storage controller 954. The image analyzer 140 may include more or less than the above components. In addition, a component may be integrated into another component. As shown in FIG. 9, all the controllers 940, 950, and 960 are integrated in the PCH 930. The integration may be partial and/or overlapped. For example, the GDC 940 may be integrated into the CPU 910, the I/O controller 960 and the memory controller 950 may be integrated into one single controller, etc.

The CPU or processor 910 is a programmable device that may execute a program or a collection of instructions to carry out a task. It may be a general-purpose processor, a digital signal processor, a microcontroller, or a specially designed processor such as one design from Applications Specific Integrated Circuit (ASIC). It may include a single core or multiple cores. Each core may have multi-way multi-threading. The CPU 910 may have simultaneous multithreading feature to further exploit the parallelism due to multiple threads across the multiple cores. In addition, the CPU 910 may have internal caches at multiple levels.

The bus 920 may be any suitable bus connecting the CPU 910 to other devices, including the PCH 930. For example, the bus 920 may be a Direct Media Interface (DMI).

The PCH 930 in a highly integrated chipset that includes many functionalities to provide interface to several devices such as memory devices, input/output devices, storage devices, network devices, etc.

The I/O controller 960 controls input devices (e.g., stylus, keyboard, and mouse, microphone, image sensor) and output devices (e.g., audio devices, speaker, scanner, printer). It also has interface to a network interface card which provides interface to a network and wireless controller (not shown).

The memory controller 950 controls memory devices such as the random access memory (RAM) and/or the read-only memory (ROM) 952, and other types of memory such as the cache memory and flash memory. The RAM 952 may store instructions or programs, loaded from a mass storage device, that, when executed by the CPU 910, cause the CPU 910 to perform operations as described above. It may also store data used in the operations. The ROM 952 may include instructions, programs, constants, or data that are maintained whether it is powered or not.

The GDC 940 controls a display device and provides graphical operations. It may be integrated inside the CPU 910. It typically has a graphical user interface (GUI) to allow interactions with a user who may send a command or activate a function. The GDC 940 may display, on the display device, images of the color lights as collected from the sample in the human body.

The mass storage controller 954 controls the mass storage devices such as CD-ROM and hard disk.

The I/O controller 960 may include another controller 962 and an optical controller 964. The other controller 962 may be a stepper motor controller or any controller that can control movement of a device such as the imaging lens 240/440/640. The optical controller 964 performs control functions related to the optical components, such as emitting light from a light source 105 to the collimator 220, etc.

Additional devices or bus interfaces may be available for interconnections and/or expansion. Some examples may include the Peripheral Component Interconnect Express (PCIe) bus, the Universal Serial Bus (USB), etc.

All or part of an embodiment may be implemented by various means depending on applications according to particular features, functions. These means may include hardware, software, or firmware, or any combination thereof. A hardware, software, or firmware element may have several modules coupled to one another. A hardware module is coupled to another module by mechanical, electrical, optical, electromagnetic or any physical connections. A software module is coupled to another module by a function, procedure, method, subprogram, or subroutine call, a jump, a link, a parameter, variable, and argument passing, a function return, etc. A software module is coupled to another module to receive variables, parameters, arguments, pointers, etc. and/or to generate or pass results, updated variables, pointers, etc. A firmware module is coupled to another module by any combination of hardware and software coupling methods above. A hardware, software, or firmware module may be coupled to any one of another hardware, software, or firmware module. A module may also be a software driver or interface to interact with the operating system running on the platform. A module may also be a hardware driver to configure, set up, initialize, send and receive data to and from a hardware device. An apparatus may include any combination of hardware, software, and firmware modules.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A spectrometer apparatus comprising:
a grating element having an interface configured to cause light beams incident to the interface to diffract in different orders, the light beams including N visible color lights where N is an integer equal to or greater than 2;
an imaging lens configured to focus the N visible color lights diffracted by the grating element, the focused N visible color lights including at least a first color light and a second color light, the first color light being diffracted in a first diffraction order and corresponding to a first wavelength resolution for the first color light, the second color light being diffracted in a second diffraction order and corresponding to a second wavelength resolution for the second color light; and
a sensor configured to receive and detect the N visible color lights focused by the imaging lens,
wherein the first diffraction order is higher than the second diffraction order and the first wavelength resolution is smaller than the second wavelength resolution.

2. The apparatus according to claim 1, wherein the first color light is a blue light and the second color light is a red light.

3. The apparatus according to claim 1, wherein the focused N visible color lights further include a third color light having a third diffraction order which is equal to or higher than the second diffraction order.

4. The apparatus according to claim 3, wherein the first color light is a blue light, the second color light is a red light, and the third color light is a green light.

5. The apparatus according to claim 1, wherein the first diffraction order is $-2^{nd}$ order and the second diffraction order is $-1^{st}$ order.

6. The apparatus according to claim 1, wherein the first color light has a wavelength band which includes one wavelength from 408 nm to 468 nm and the second color light has a wavelength band which includes one wavelength from 680 nm to 780 nm.

7. The apparatus according to claim 1, wherein the third color light has a wavelength band which includes one wavelength from 510 nm to 580 nm.

8. The apparatus according to claim 1, wherein the grating element has binary grating, blazed grating, or holographic grating.

9. The apparatus according to claim 1, wherein the grating element is of a transmission or reflection type.

10. The apparatus according to claim 1, further comprising:
    an image analyzer configured to display an image collected from the N visible color lights detected by the sensor.

11. A method to provide high resolution color spectrometer for spectrally-encoded endoscopy (SEE) imaging system, the spectrometer having optical parameters of components configured to perform operations comprising:
    causing light beams incident to an interface of a grating element to diffract at different orders, the light beams including N visible color lights where N is an integer equal to or greater than 2;
    focusing, by an imaging lens, the N visible color lights diffracted by the grating element, the focused N visible color lights including at least a first color light and a second color light, the first color light being diffracted in a first diffraction order and corresponding to a first wavelength resolution for the first color light, the second color light being diffracted in a second diffraction order and corresponding to a second wavelength resolution for the second color light; and
    receiving and detecting, by a sensor, the N visible color lights focused by the imaging lens,
    wherein the first diffraction order is higher than the second diffraction order and the first wavelength resolution is smaller than the second wavelength resolution.

12. The method according to claim 11, wherein the first color light is a blue light and the second color light is a red light.

13. The method according to claim 11, wherein the focused N visible color lights further include a third color light having a third diffraction order which is equal to or higher than the second diffraction order.

14. The method according to claim 13, wherein the first color light is a blue light, the second color light is a red light, and the third color light is a green light.

15. The method according to claim 11, wherein the first diffraction order is $-2^{nd}$ order and the second diffraction order is $-1^{st}$ order.

16. The method according to claim 11, wherein the first color light has a wavelength band which includes one wavelength from 408 nm to 468 nm and the second color light has a wavelength band which includes one wavelength from 680 nm to 780 nm.

17. The method according to claim 11, wherein the third color light has a wavelength band which includes one wavelength from 510 nm to 580 nm.

18. The method according to claim 11, wherein the grating element has binary grating, blazed grating, or holographic grating.

19. The method according to claim 11, wherein the grating element is of a transmissive or reflective type.

20. The method according to claim 11, wherein the optical parameters include at least one of a focal length of the imaging lens, a groove density of the grating element, a diameter of an input fiber core as guiding element for the light source of the incident light beams, and an incident angle on the grating element.

21. A system comprising:
    a light source that generates light beams; and
    a spectrometer subsystem to image high resolution color lights from the light beams, the spectrometer subsystem comprising:
        a collimation lens configured to collimate the light beams;
        a grating element having an interface configured to cause the light beams incident to the interface to diffract at different orders, the light beams including N visible color lights where N is an integer equal to or greater than 2;
        an imaging lens configured to focus the N visible color lights diffracted by the grating element, the focused N visible color lights including at least a first color light and a second color light, the first color light being diffracted in a first diffraction order and corresponding to a first wavelength resolution for the first color light, the second color light being diffracted in a second diffraction order and corresponding to a second wavelength resolution for the second color light; and
        a sensor configured to receive and detect the N visible color lights focused by the imaging lens,
        wherein the first diffraction order is higher than the second diffraction order and the first wavelength resolution is smaller than the second wavelength resolution.

* * * * *